United States Patent
Wang et al.

(10) Patent No.: US 9,226,838 B2
(45) Date of Patent: Jan. 5, 2016

(54) ABSORBABLE BLOOD VESSEL STENT

(75) Inventors: Yongsheng Wang, Shenzhen (CN);
Deyuan Zhang, Shenzhen (CN);
Chaohua Xin, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 237 days.

(21) Appl. No.: 13/995,101

(22) PCT Filed: Dec. 8, 2011

(86) PCT No.: PCT/CN2011/083683
§ 371 (c)(1),
(2), (4) Date: Jul. 16, 2013

(87) PCT Pub. No.: WO2012/083796
PCT Pub. Date: Jun. 28, 2012

(65) Prior Publication Data
US 2013/0325102 A1    Dec. 5, 2013

(30) Foreign Application Priority Data

Dec. 21, 2010   (CN) .......................... 2010 1 0598542

(51) Int. Cl.
| | | |
|---|---|---|
| A61F 2/06 | (2013.01) | |
| A61F 2/89 | (2013.01) | |
| A61L 31/14 | (2006.01) | |
| A61F 2/91 | (2013.01) | |
| A61L 31/02 | (2006.01) | |

(52) U.S. Cl.
CPC ... *A61F 2/89* (2013.01); *A61F 2/91* (2013.01); *A61L 31/022* (2013.01); *A61L 31/14* (2013.01); *A61L 31/148* (2013.01); *A61F 2210/0004* (2013.01)

(58) Field of Classification Search
CPC ..... A61L 31/148; A61L 31/022; A61L 31/14; A61F 2/82; A61F 2210/0004; A61F 2/90; A61F 2/89; A61F 2/915; A61F 2/91
USPC ....................... 623/1.15, 1.16, 1.38
See application file for complete search history.

(56) References Cited

U.S. PATENT DOCUMENTS

| | | | |
|---|---|---|---|
| 6,287,332 B1* | 9/2001 | Bolz et al. ............... | 623/1.15 |
| 2006/0106452 A1* | 5/2006 | Niermann ............... | 623/1.15 |
| 2010/0292777 A1* | 11/2010 | Meyer et al. ............ | 623/1.16 |
| 2012/0029623 A1* | 2/2012 | Baillargeon ............ | A61F 2/915 |
| | | | 623/1.16 |

\* cited by examiner

*Primary Examiner* — Katherine M Shi
(74) *Attorney, Agent, or Firm* — Raymond Sun

(57) ABSTRACT

An absorbable blood vessel stent (100) has a near end and a far end. A tubular patterned structure is formed between the near end and the far end. The patterned structure comprises a plurality of support bars and connection bars (2, 3). The support bar or the connection bar (2, 3) comprises a straight line section, a U-shaped section, or an S-shaped section, and at least one through groove or through hole (5, 6) is provided on at least one support bar. Because of the special structure of the blood vessel stent (100), the performance of an iron blood vessel stent can be improved, and blood vessel stents made of other absorbable materials can be decomposed more rapidly.

14 Claims, 3 Drawing Sheets

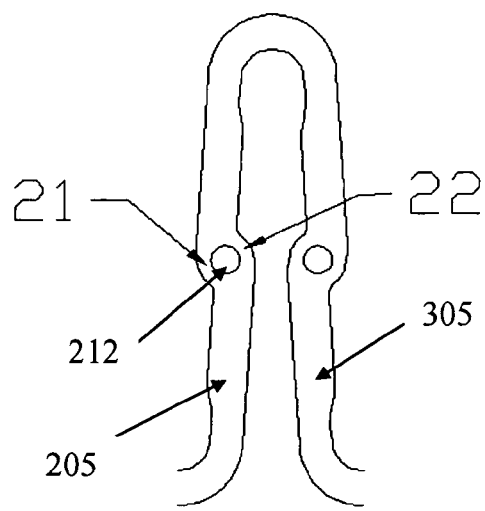
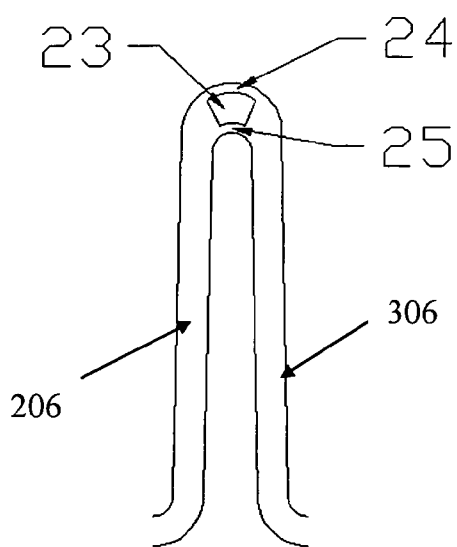
Figure 8
Figure 9
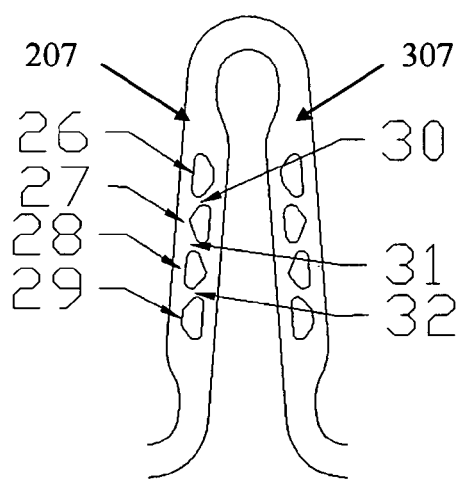
Figure 10

ABSORBABLE BLOOD VESSEL STENT

TECHNICAL FIELD

The invention relates to a medical instrument, and in particular, to an absorbable blood vessel stent for treatment of blood vessel lumen stenosis.

BACKGROUND OF THE INVENTION

In 1977, the first case of Percutaneous Coronary Intervention (PCI) surgery in the world was accomplished in Switzerland. In this surgery, a balloon was employed to dilate the position of the left anterior descending branch stenosis of the patient, successfully. However, the re-stenosis rate of the blood vessel after balloon dilation was very high, over 50%. The main reason was that, after the blood vessel was dilated and the external force was removed, the blood vessel may elastically recoil. In the 1980s, blood vessel stents widely used for coronary artery were invented. There were blood vessel metal stents mainly made of stainless steel, cobalt-chromium alloy or nickel-titanium alloy. After implanted into the human body, the stents may provide durable mechanical support for the blood vessel, thereby preventing the blood vessel from elastically recoiling and reducing the re-stenosis rate of the diseased blood vessel. However, since the stents were permanently implanted into the human body, the stents as foreign substances may cause intimal hyperplasia and quite high re-stenosis rate of the blood vessel. Since 2003, the application of the drug stents reduces the blood vessel re-stenosis rate to about 10%. However, since the drug stents still existed inside the human body permanently, the stents as foreign matter have great differences with vascular tissues in terms of mechanical property, which may cause chronic injury of the blood vessel, cause blood vessel medial atrophy and intimal hyperplasia at the late stage, and may also cause blood vessel re-stenosis finally, thereby limiting the further reduction of the blood vessel re-stenosis rate. As for children, the implantation of blood vessel stents with fixed sizes may hinder the gradual increase of the blood vessel, being unable to meet the requirement on the growth of children.

Both of the above intervention treatment technologies for blood vessel stenosis have defects: for dilating the blood vessel by using balloons, although the short-term effect is good, the re-stenosis rate at the late stage is very high because of elastic recoiling of the blood vessel; for implanting metal stents into the blood vessel, the metal stents including bare stent and drug stent may dilate the narrow blood vessel and provide a durable mechanical support, however, the blood vessel intima may be injured during the dilation of the metal stents, which may induce blood vessel intimal hyperplasia to lead to re-stenosis. The metal stents further have the defects of thrombosis, coagulation complication, flexibility mismatching, and increase of the re-stenosis occurrence rate at late stage if permanently remaining inside the human body.

In order to solve the above problems, in recent years, many people have begun to pay close attention to blood vessel stents that are absorbable by the human body. After a blood vessel stent is implanted into the human body, the ideal situation should be that, at the initial stage, the blood vessel stent provides a sufficient support to the blood vessel, and meanwhile releases drugs to treat the diseased blood vessel, and after the treating function is accomplished, the blood vessel stent is gradually absorbed so as to prevent the re-stenosis. According to different materials, there are two main kinds of absorbable blood vessel stents, one kind is the blood vessel stent made of macromolecular polymer materials, such as polylactic acid; and the other kind is the blood vessel stent made of metal materials, such as magnesium alloy and iron.

Recently, many people have been doing research on making blood vessel stents, for example, a polylactic acid stent, by degradable macromolecular materials, and some research results have started clinical tests. However, compared with the metal materials, the degradable macromolecular materials have obvious defects in terms of mechanical property, and so the application thereof is limited. When compared with the metal materials, the macromolecular polymer materials have low mechanical property and insufficient strength. In order to achieve certain radial support, the wall thickness of the stent must be increased. However, after implantation inside the human body, the stent with a thick wall may hinder the flow of the blood. In addition, the retraction rate of the macromolecular polymer material stents is quite high after dilation by the balloons, and so the expansion ratio of the diameter of the stent after dilated with respect to the diameter of the blood vessel is larger than that of the metal material stents, which may cause greater injury to the blood vessel during the dilation. The X-ray visibility of the macromolecular polymer material stents inside the human body is poor, and so it is difficult to locate and observe the stents during the implantation.

At present, there are mainly two types of metal materials applied to absorbable blood vessel stents: magnesium alloy material and pure iron material. The magnesium alloy material is poor in mechanical property and corrodes quickly. The magnesium alloy material has good bio-compatibility. However, the maximum elongation rate of the magnesium alloy stents is low, which brings great challenge to the structural design of the magnesium alloy stents, and so it is difficult to ensure the good mechanical property of the stents. Furthermore, the corrosion rate of the magnesium alloy stents is too fast, so a complex material manufacture process must be adopted to control the rate by which the magnesium alloy stents are absorbed by the human body. Iron is an essential element for the human body, and simultaneously, pure iron has good bio-compatibility and mechanical property. Compared with the polymer stents or magnesium alloy stents having a same wall thickness, the iron stents may provide a sufficient radial support for the diseased blood vessel at the diseased position. However, the corrosion rate of the pure iron is relatively slow, the iron stents of common structure design may be absorbed by the human body after a long time, during which process the diameter of the blood vessel may be restrained, so it cannot meet the requirement on the gradual increase of the blood vessel for children.

Therefore, how to design a blood vessel stent that can accelerate the absorption process of the human body and simultaneously ensure the mechanical property thereof is an urgent problem to be solved at present.

DISCLOSURE OF THE INVENTION

Technical Problem

The technical problem to be solved in the invention is to provide a blood vessel stent which is used for treating blood vessel stenosis and is absorbable by the human body, so as to solve the problem in the prior art that the two properties, that is, the mechanical property of the absorbable blood vessel stents and the blood vessel stent being absorbed as fast as possible, are hard to be balanced.

SUMMARY OF THE INVENTION

The technical solutions for solving the technical problem of the invention are as follows: an absorbable blood vessel stent is provided, having a near end and a far end, a pattern structure that is tubular and dilatable is formed between the near end and the far end, the pattern structure comprises a plurality of support bars and connection bars, the connection bar or support bar comprises a linear section, a U-shaped section, or an S-shaped section, and at least one through groove or through hole is provided on at least one support bar.

As a further improvement on the absorbable blood vessel stent of the invention, the support bar has at least one neck portion, the neck portion is located near the through groove or through hole, and the neck portion has the minimum width on the support bar.

As a further improvement on the absorbable blood vessel stent of the invention, one or more through grooves parallel to the linear section are provided on the linear section of the support bar, any one of the through grooves and the linear section form two branches, the branches have the minimum width on the support bar; and the plurality of through grooves are arrayed along the support bar with a beam arranged between the adjacent through grooves, and the beam has the minimum width on the support bar.

As a further improvement on the absorbable blood vessel stent of the invention, a neck portion is formed at an end of the branch, the neck portion has the minimum width on the support bar; and a broad portion is formed at the other end of the branch, and the broad portion has the maximum width on the branch.

As a further improvement on the absorbable blood vessel stent of the invention, the support bar or the joint of two support bars has a curved section thereon, and at least one through hole is provided on the curved section.

As a further improvement on the absorbable blood vessel stent of the invention, the support bar comprises at least one truss structure, the truss structure comprises a plurality of through grooves or through holes, a beam is arranged between the adjacent through grooves or through holes, the truss structure further has a plurality of side beams on both sides thereof, and the beam and the side beam have the minimum width on the support bar.

As a further improvement on the absorbable blood vessel stent of the invention, the pattern structure further comprises several circles of wave sections where two adjacent circles of wave sections are coupled to connect, the wave sections are connected by the connection bars of the pattern structure, each circle of wave section comprises a plurality of arched support pieces connected head to tail and a plurality of wave valleys, two adjacent arched support pieces are connected by a wave valley, the arched support piece comprises a wave peak, a first support bar, and a second support bar, and the first support bar and the second support bar are connected by the wave peak; and the at least one through groove or through hole is provided at the first support bar, the second support bar, the wave peak or wave valley.

As a further improvement on the absorbable blood vessel stent of the invention, the first support bar and the second support bar are symmetric with each other.

As a further improvement on the absorbable blood vessel stent of the invention, the minimum width on the support bar is 0.05-0.1 mm.

As a further improvement on the absorbable blood vessel stent of the invention, the blood vessel stent is made of iron or iron alloy material.

Beneficial Effects

Compared with the prior art, the invention has the following advantages: 1. the absorbable blood vessel stent of the invention with a special structure can be corroded and disassembled only within a short time, which reduces the restenosis probability of the diseased blood vessel, contributes to continuous growth and expansion after the repair of the diseased blood vessel, and meets requirements of clinical use; 2. the structure of the absorbable blood vessel stent of the invention does not sacrifice the mechanical property of the blood vessel stent when promoting the corrosion and disassembly of the blood vessel stent, the blood vessel stent maintains the sufficient radial support force for the diseased blood vessel before disassembly; and 3. the absorbable blood vessel stent of the invention may be made of an iron pipe, the wall thickness of the blood vessel stent is not increased compared with a common permanent blood vessel stent, and the stent may be conveyed by adopting a balloon catheter which is commonly used for clinical application, and so cost of clinical promotion of absorbable blood vessel stent is reduced, and the clinically applicable scope of the absorbable blood vessel stent is extended.

BRIEF DESCRIPTION OF THE DRAWINGS

FIG. 8 is a schematic diagram of a fifth embodiment of an arched support piece of a circle of wave section in FIG. 3;

FIG. 9 is a schematic diagram of a sixth embodiment of an arched support piece of a circle of wave section in FIG. 3; and FIG. 10 is a schematic diagram of a seventh embodiment of an arched support piece of a circle of wave section in FIG. 3.

DETAILED DESCRIPTION OF THE INVENTION

To make the purposes, technical solutions and advantages of the invention more clear, the invention will be further described in details as below by embodiments with reference to the drawings. It should be understood that the specific embodiments described herein are only used for explaining the invention, but not for limiting the invention.

Figure 1:
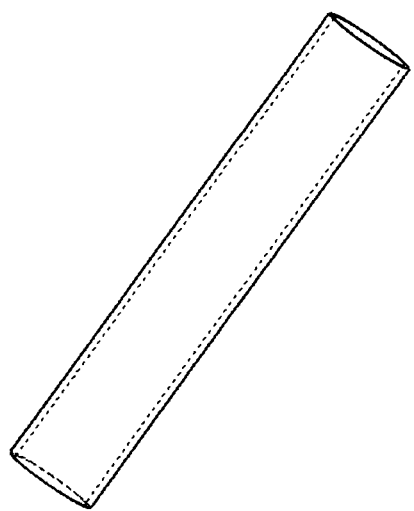
FIG. 1 is a schematic diagram of an absorbable blood vessel stent prior to laser engraving molding according to the present invention.
Figure 2:
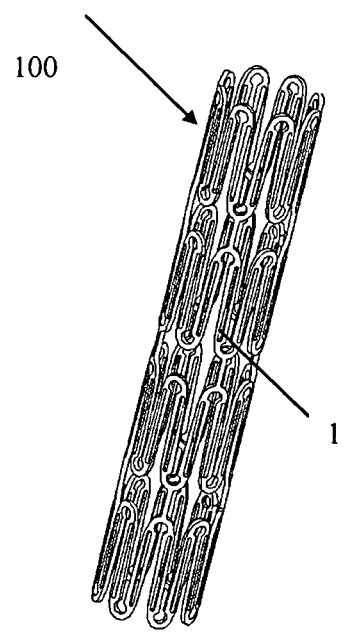
FIG. 2 is a schematic diagram of an absorbable blood vessel stent that is not dilated yet after laser engraving according to the present invention.

As shown in FIG. 1, the absorbable blood vessel stent in the first embodiment of the invention is a thin iron pipe with a diameter of 2 mm and a wall thickness of 0.1 mm before laser engraving. FIG. 2 shows a blood vessel stent 100 that is formed after the iron pipe is engraved by laser and that is not dilated yet. The blood vessel stent 100 has a near end and a far end, a dilatable pattern structure exists between the near end and the far end, and the stent consists of four annular connected wave sections in total, each annular wave section is formed by eight arched support pieces which are connected head to tail to form a circle, and each circle of the wave section is connected to another by linear connection bars 1. It may be understood that, the blood vessel stent 100 may also consist of two circles of, three circles of, five circles of or more circles of connected wave sections, and there may also be more than or less than eight arched support pieces included in each annular wave section. The connection bar 1 may also be in another shape, such as U shape or S shape. The blood vessel stent 100 may also be made of iron alloy or other materials. Based on the common technology in this art, the pattern structure used in a known absorbable blood vessel stent or other blood vessel stents, as long as it consists of support bars and connection bars, can be used for the absorbable blood vessel stent of the invention and be in accordance with the principle of the invention, and only the support bars therein need to be treated in the same way.

Figure 3:
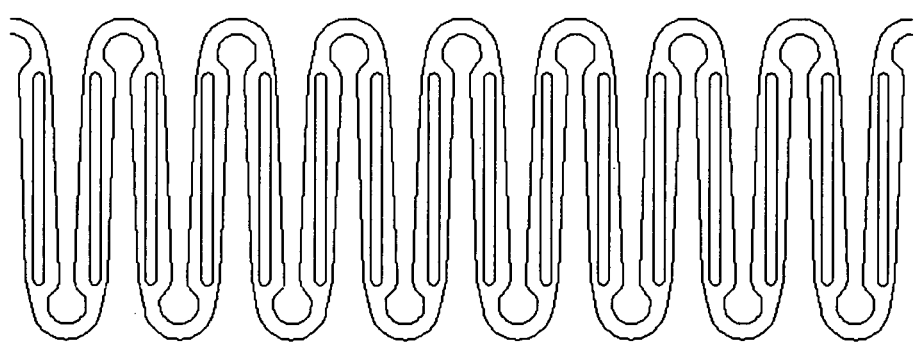
FIG. 3 is a plane diagram of a circle of wave section of the blood vessel stent in FIG. 2.
Figure 4:
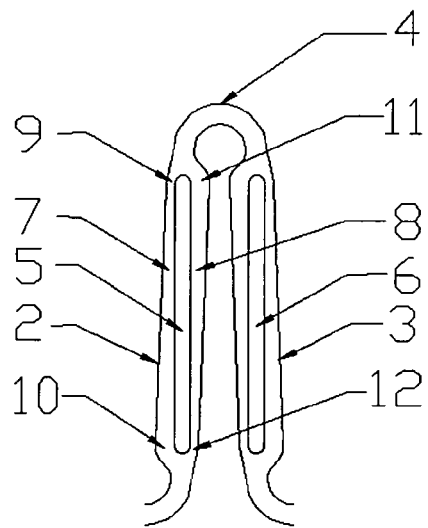
FIG. 4 is a schematic diagram of a first embodiment of an arched support piece of a circle of wave section in FIG. 3.

FIG. 3 is a plane diagram of a circle of wave section after the blood vessel stent 100 is slightly dilated radially, and FIG. 4 is a first embodiment of an arched support piece of the circle of wave section. The arched support piece comprises a first support bar 2 and a second support bar 3 with an angle to each other, and the first support bar 2 and the second support bar 3 essentially are single linear sections and are connected by the wave peak 4 at the top of the arch. In order to make the blood vessel stent have different properties, the first support bar 2 and the second support bar 3 may be symmetric, or may also be asymmetric. The support bar may not only be in the shape of single linear section shown in FIG. 4, but also be in a curved shape containing several linear sections, for example, U shape, S shape, or a combination of these shapes and other shapes, and only the linear sections therein need to be treated in a similar manner. Adjacent arched support pieces are connected by the wave valley at the bottom, and the wave valley contained by a wave section may be connected with a wave peak contained by the adjacent wave section by the connection bar 1. The wave peak of a single wave section is closer to the far end of the stent than the wave valley. The wave peak 4 and wave valley may be in different shapes, and may also be in symmetrical structures. A first through groove 5 is provided in the middle part of the first support bar 2, a second through groove 6 is provided in the middle part of the second support bar 3, and both ends of the first through groove 5 and the second through groove 6 are respectively close to positions of the wave peak 4 and the wave valley which are connected with corresponding support bars. The first through groove 5 divides the middle part of the first support bar 2 into a first branch 7 and a second branch 8. A neck portion 9 is provided at the position where the first branch 7 is close to the wave peak 4, and the neck portion 9 is the position with the minimum width on the first branch 7, wherein the minimum width may be chosen from 0.05 mm-0.1 mm. A broad portion 10 is arranged at the other end of the first branch 7, and is the position with the maximum width on the first branch 7, wherein the width of the broad portion 10 may be chosen from 0.1-0.2 mm. On the first branch 7, the width from the neck portion 9 to the broad portion 10 may change gradually. Another broad portion 11 is provided at the position opposite to the neck portion 9 on the second branch 8, and the width may be chosen from 0.1-0.2 mm, and the broad portion 11 is the position with the maximum width on the second branch 8. Another neck portion 12 with a width between 0.05 mm-0.1 mm is provided at the position opposite to the broad portion 10 on the second branch 8, and is the position with the minimum width on the second branch 8. On the second branch 8, the width may change gradually from the neck portion 12 to the broad portion 11. When the blood vessel stent 100 is dilated and deformed, since the strength of the broad portions 10 and 11 is larger than the strength of the neck portions 9 and 12, the broad portion 11 may protect the neck portion 9 from large deformation, and the broad portion 10 may protect the neck portion 12 from large deformation. After the blood vessel stent 100 is implanted into the body, since the neck portions 9 and 12 are respectively the parts with the minimum widths on the first branch 7 and the second branch 8, the neck portion 9 and the neck portion 12 may break first because of corrosion, which causes the first support bar 2 to completely break, and the blood vessel stent 100 may disassemble at this place in a shorter time. The second support bar 3 has the structure and technical effect similar to the first support bar 2, and breaks in the human body after an approximately same time of corrosion.

During the process that the stent is dilated, the first branch 7 and the second branch 8 located at both sides of the through groove 5 may be deformed simultaneously. The broad portion 11 is close to and aligned with the neck portion 9. The width of the broad portion 11 is larger, and so it is hard to be deformed during the dilation process. Therefore, the stress for deforming the first support bar 2 is mainly distributed at the broad portion 11, while the neck portion 9 at the opposite side receives a smaller force. That is to say, the neck portion 9 may avoid large deformation because of the protection of the broad portion 11. Under the cooperation of the first branch 7 and the second branch 8, the first support bar 2 still keeps a good mechanical property. Therefore, the through groove 5 does not do harm to the overall mechanical property of the iron blood vessel stent.

Figure 5:
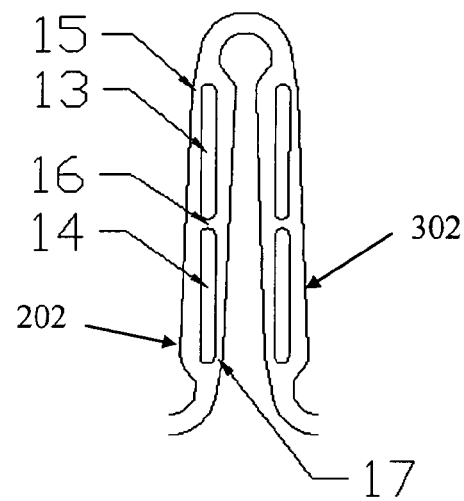
FIG. 5 is a schematic diagram of a second embodiment of an arched support piece of a circle of wave section in FIG. 3.

FIG. 5 is a schematic diagram of a second embodiment of an arched support piece on the absorbable blood vessel stent of the invention, which is roughly same with the first embodiment, and the differences lie in that: two longitudinally arranged through grooves 13 and 14 are arranged on the first support bar 202, and divide the first support bar 202 into two branches, and two longitudinally arranged through grooves similar to the through grooves 13 and 14 are also arranged on the second support bar 302 which is connected with the first support bar 202, and also divide the second support bar 302 into two branches. Likewise, a neck portion 15 is arranged at the end where a branch is close to the wave peak, another neck portion 17 is arranged at the opposite end of the other branch. A beam 16 exists between the through groove 13 and the through groove 14 to separate the through groove 13 and the through groove 14. The width of the beam 16 in the peripheral direction of the blood vessel stent 100 is the same as the widths of the neck portion 15 and the neck portion 17, and is the minimum width on the first support bar 202. Neck portions which are as wide as the neck portions 15 and 17 are also respectively arranged at the corresponding positions of the both branches on the second support bar 302, and the two through grooves are also separated by another beam as wide as the beam 16. Using a beam to connect two branches of the support bar may increase the structural strength and stability of the support bar. The blood vessel stent 100 starts corrosion when implanted into the human body, for the first support bar 202, the neck portions 15 and 17 and the beam 16 with the minimum width may break first, which causes the first support bar 202 to completely break. Since the second support bar 302 has a structure and size similar to the first support bar 202, the two support bars may simultaneously and completely break, so that the blood vessel stent 100 may disassemble at this place in a shorter time.

Figure 6:
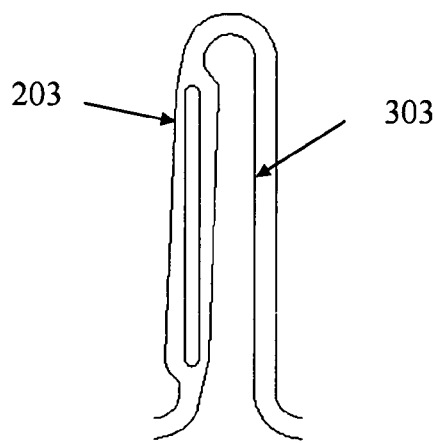
FIG. 6 is a schematic diagram of a third embodiment of an arched support piece of a circle of wave section in FIG. 3.

FIG. 6 is a schematic diagram of a third embodiment of an arched support piece on the absorbable blood vessel stent of the invention, the first support bar 203 of the support piece is the same as the first support bar 2 in the first embodiment of the support piece in shape and structure, the support piece also has a second support bar 303, but the difference lies in that, no through groove is provided on the second support bar 303. Compared with the first embodiment, the third embodiment may improve the overall strength of the blood vessel stent, while the time from corrosion to disassembly of the blood vessel stent inside the human body is almost the same.

Figure 7:
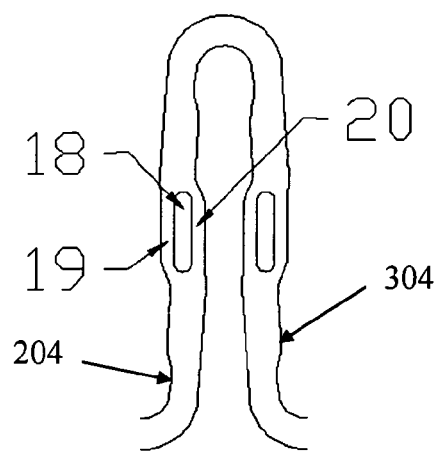
FIG. 7 is a schematic diagram of a fourth embodiment of an arched support piece of a circle of wave section in FIG. 3.

FIG. 7 is a schematic diagram of a fourth embodiment of an arched support piece on the absorbable blood vessel stent of the invention. The fourth embodiment of the support piece is similar to the first embodiment, and the differences lie in that: the middle section of the first support bar 204 of the support piece is a linear section, a through groove 18 shorter than the through groove 13 is provided at the middle position of the linear section, and it is preferred to set the length of the through groove 18 to be one to three times of the width of the first support bar 204; and another through groove similar to the through groove 18 is also provided at the middle position of the second support bar 304. The through groove 18 divides the linear section of the first support bar 204 into two branches, that is, a first branch 19 and a second branch 20, the two branches are the parts having the minimum width on the support bar 204, that is, the neck portions. The first branch 19 and the second branch 20 will break first when the blood vessel stent is corroded, which causes the first support bar 204 to break completely. The second support bar 304 has effects similar to the first support bar 204, and also has a similar through groove and branches, and the two support bars may simultaneously fully break, so that the blood vessel stent may disassemble at this place in a shorter time. Since the through groove 18 herein is quite short and has a small effect on the structural strength of the support bar, the broad portions in the first embodiment are unnecessary. In addition, the widths of the first branch 19 and the second branch 20 may be substantially uniform, the widths thereof may be equal, and are chosen from the range of 0.05-0.1 mm.

FIG. 8 is a schematic diagram of a fifth embodiment of an arched support piece on the absorbable blood vessel stent of the invention. The fifth embodiment of the support piece is similar to the fourth embodiment, and the differences lie in that: the slightly S-shaped first support bar 205 of the support piece has a S-shaped curved section at the middle position thereof, a round or approximately round through hole 212 is arranged at this place, the second support bar 305 is also slightly S-shaped, and also has such a through hole in the middle position thereof, and so the strength of the first support bar 205 and the second support bar 305 is better than that of fourth embodiment. Neck portions 21 and 22 are respectively arranged at both sides of the through hole 212. The widths of the neck portions 21 and 22 are the minimum widths on the first support bar 205, such as 0.05 mm. The positions of the neck portions 21 and 22 will be first corroded and break, which causes the first support bar 205 to break completely. Like the first support bar 205, similar neck portions with the minimum widths are arranged at both sides of the through hole of the second support bar 305, so that the blood vessel stent can break and disassemble in a shorter time.

FIG. 9 is a schematic diagram of a sixth embodiment of an arched support piece on the absorbable blood vessel stent of the invention. The sixth embodiment of the support piece is similar to the third embodiment, and the differences lie in that: no through grooves are provided on the first support bar 206 and the second support bar 306 of the support piece, an approximate fan-shaped through hole 23 is provided at the wave peak connecting the first support bar 206 and the second support bar 306. The through hole 23 divides the wave peak into two arched portions with small widths, that is, a first arched portion 24 at the outer side and a second arched portion 25 at the inner side, the radial widths of the first arched portion 24 and the second arched portion 25 are basically equal, and the first arched portion 24 and the second arched portion 25 are the positions with the minimum widths of the whole support piece, that is, are neck portions, and the widths thereof are approximately 0.05-0.1 mm. Therefore, when the blood vessel stent is corroded inside the human body, the two arched portions 24 and 25 will break first, which causes the support piece to break completely at the wave peak, so that the blood vessel stent can disassemble at this place in a shorter time. Adjacent arched support pieces are connected by a wave valley, and so structures similar to the through hole 23, the first arched portion 24, and the second arched portion 25 can be arranged at the wave valley. Since the blood vessel stent is corroded, the adjacent arched support pieces are disconnected at the wave valley in a shorter time. If the blood vessel stent adopts a pattern structure of another form, similar through groove, outer arched portion, and inner arched portion may also be arranged at the curved position of the support bar. When the blood vessel stent is dilated, the stress at the inner side is larger than the stress at the outer side of the wave peak or wave valley. Therefore, the second arched portion 25 at the inner side may be wider than the first arched portion 24 at the outer side, so as to enable the whole arched support piece to keep a good mechanical property.

FIG. 10 is a schematic diagram of a seventh embodiment of an arched support piece on the absorbable blood vessel stent of the invention. The seventh embodiment of the support piece is similar to the second embodiment, and the differences lie in that: a truss structure composed of a plurality of segments of beam arms is arranged at the middle position of the first support bar 207, the truss structure forms four through holes 26, 27, 28, and 29, beams 30, 31, and 32 are formed between the through holes 26, 27, 28, and 29, and the second support bar 307 also has a similar truss structure at the middle position thereof. Several side beams are provided at the outer side of the middle position of the first support bar 207 and the second support bar 307, and each side beam and beam 30, 31, and 32 has the minimum width on the support bar, for example, the width may be chosen from 0.05-0.1 mm. On the premise that the arched support piece has a higher structural strength and mechanical stability, the truss structures at the middle positions of the first support bar 207 and the second support bar 307 enable the blood vessel stent to use minimum materials. Since the truss structure reduces the amount of metal used, it is easier for the blood vessel stent to be absorbed completely by the human body in a shorter time; and the existence of each through hole increases the surface area of the blood vessel stent, the corrosion area is increased, and thus the disassembly of the blood vessel stent is accelerated.

In the absorbable blood vessel stent for treating blood vessel stenosis provided in the invention, the special structure thereof not only can improve the properties of the iron blood vessel stent, but also can accelerate the corrosion and disassembly of the blood vessel stent made of other absorbable materials. After blood vessel intimal cells wholly wrap the blood vessel stent, particular positions of this kind of blood vessel stent can be corroded in a shorter time, so as to make the whole blood vessel stent break into several parts in the peripheral direction. In this way, the radial restraint of the blood vessel stent for the blood vessel is removed, and thus normal increase of the blood vessel at this place will not be hindered. Further, since the blood vessel stent is divided into several parts after disassembly, and is wrapped by intimal cells, the remnant structures are smaller, which helps the vascular tissues absorb the remnant parts of the blood vessel stent. The blood vessel stent of this structure does not weaken the overall mechanical property of the blood vessel stent, and the radial support force before disassembly can still meet the requirement of the diseased blood vessel. With the blood vessel stent of the invention, the time that the human body absorbs the stent is reduced, and meanwhile, the blood vessel stent is ensured to have a sufficient mechanical property.

Compared with the prior art, the invention has the following advantages: 1. the absorbable blood vessel stent of a special structure of the invention may be corroded and disassembled only within a short time, which reduces the restenosis probability of the diseased blood vessel, contributes to continuous growth and expansion after the repair of the diseased blood vessel, and meets requirements on clinical use; 2. the structure of the absorbable blood vessel stent of the invention does not sacrifice the mechanical property of the blood vessel stent when promoting the corrosion and disassembly of the blood vessel stent, the blood vessel stent maintains the sufficient radial support force for the diseased blood vessel before disassembly; and 3. the absorbable blood vessel stent of the invention may be made of an iron pipe, the wall thickness of the blood vessel stent is not increased compared with a common permanent blood vessel stent, and the stent may be conveyed by adopting a balloon catheter which is commonly used for clinical application, so the cost of clinical promotion of absorbable blood vessel stent is reduced, and the clinically applicable scope of the absorbable blood vessel stent is extended.

The above contents just describe the preferred embodiments of the invention, provided not for limiting the present invention. Any modifications, equivalent replacements and improvements made within the spirit and principle of the invention should fall into the protection scope of the invention.

The invention claimed is:

1. A stent having an annular pattern structure comprising a plurality of support bars, each support bar having opposite first and second ends, with each support bar connected to a separate adjacent support bar at its first and second ends by a wave peak, wherein at least one support bar has first and second branches, with each branch having a first end and an opposing second end, with each first branch having a minimum width at the first end of the first branch and a maximum width at the second end of the first branch, and each second branch having a maximum width at the first end of the second branch and a minimum width at the second end of the second branch; and wherein the width of the first branch from the first end of the first branch to the second end of the first branch change wider gradually, and the first end of the first branch is nearer to the first end of the second branch than the second end of the second branch.

2. The stent of claim 1, wherein the stent is an absorbable blood vessel stent and the annular pattern structure is dilatable.

3. The stent of claim 1, wherein each support bar is in the shape of single linear section, and the first and second branches of the support bar is provided in the middle part thereof.

4. The stent of claim 3, wherein a first support bar of the plurality of support bars is symmetric with its adjacent support bar.

5. The stent of claim 3, wherein a first support bar of the plurality of support bars having the first branch and the second branch further comprises a beam connecting the first and second branches thereof to define two grooves between the first and second branches thereof.

6. The stent of claim 3, wherein the minimum width is 0.05-0.1 mm.

7. The stent of claim 3, wherein the stent is made of iron or iron alloy material.

8. The stent of claim 1, wherein a first support bar of the plurality of support bars having the first branch and the second branch further comprises a beam connecting the first and second branches thereof to define two grooves between the first and second branches thereof.

9. The stent of claim 1, wherein the minimum width is 0.05-0.1 mm.

10. A stent having an annular pattern structure comprising a plurality of support bars, each support bar having opposite first and second ends, with each support bar connected to a separate adjacent support bar at its first and second ends by a wave peak, wherein at least one support bar has first and second branches, with each branch having a neck portion and an opposing broad portion, with each first branch having a minimum width at the neck portion thereof and a maximum width at the broad portion thereof, each second branch having a maximum width at the broad portion thereof and a minimum width at the neck portion thereof, the neck portion of the first branch is nearer to the broad portion of the second branch than the neck portion of the second branch; and wherein the width of the first branch from the neck portion of the first branch to the broad portion of the first branch change wider gradually.

11. The stent of claim 10, wherein the stent is an absorbable blood vessel stent and the annular pattern structure is dilatable.

12. The stent of claim 11, wherein a first support bar of the plurality of support bars is in the shape of single linear section, and the first and second branches of the support bar is provided in the middle part thereof.

13. The stent of claim 12, wherein the first support bar of the plurality of support bars having the first branch and the second branch further comprises a beam connecting the first and second branches thereof to define two grooves between the first and the second branches thereof.

14. The stent of claim 11, wherein a first support bar of the plurality of support bars having the first branch and the second branch further comprises a beam connecting the first and second branches thereof to define two grooves between the first and the second branches thereof.

* * * * *